United States Patent
Bodenschatz et al.

(10) Patent No.: US 6,350,247 B2
(45) Date of Patent: Feb. 26, 2002

(54) BANDAGE FOR THE ANKLE JOINT

(75) Inventors: Stefan Bodenschatz, Buxtehude; Brigitte Rosenbaum, Hamburg, both of (DE)

(73) Assignee: Beiersdorf AG, Hamburg (DE)

( * ) Notice: Subject to any disclaimer, the term of this patent is extended or adjusted under 35 U.S.C. 154(b) by 0 days.

(21) Appl. No.: 09/233,833

(22) Filed: Jan. 20, 1999

(30) Foreign Application Priority Data

Jan. 23, 1998 (DE) .......................... 198 02 511

(51) Int. Cl.⁷ .............................. A61F 5/00; A61F 13/00
(52) U.S. Cl. ............................ 602/65; 602/27; 128/882
(58) Field of Search .................... 602/27, 23, 60–62, 602/65, 63, 75, 5; 128/882, 892, 893, 894

(56) References Cited

U.S. PATENT DOCUMENTS

| | | | |
|---|---|---|---|
| 1,030,861 A | * 7/1912 | Anderson | 602/65 |
| 1,595,087 A | * 8/1926 | Gibson | |
| 1,812,149 A | * 6/1931 | Hoggson | |
| 2,013,757 A | * 9/1935 | Jung, Jr. | 602/65 |
| 2,539,170 A | * 1/1951 | Waite | 602/62 |
| 3,699,959 A | 10/1972 | Garrahan et al. | 128/166 |
| 3,766,385 A | * 10/1973 | Buese | 602/7 |
| 3,777,751 A | 12/1973 | Wise | 128/166 |
| 4,085,746 A | 4/1978 | Castiglia | 128/166 |
| 4,367,733 A | * 1/1983 | Stromgren | 602/65 |
| 4,597,395 A | * 7/1986 | Barlow et al. | 602/27 |
| 4,753,228 A | 6/1988 | Selner et al. | 128/80 |
| 4,962,768 A | * 10/1990 | Stromgren | 602/27 |
| 5,067,486 A | * 11/1991 | Hely | 602/27 |
| 5,092,318 A | * 3/1992 | More et al. | 602/65 X |
| 5,139,479 A | * 8/1992 | Peters | 602/65 X |
| 5,209,801 A | * 5/1993 | Smith | 156/161 |

FOREIGN PATENT DOCUMENTS

| | | | |
|---|---|---|---|
| DE | 31 22 463 A1 | 12/1982 | A61F/13/06 |
| DE | 31 22 463 C2 | 12/1982 | A62F/13/06 |
| DE | 34 15 657 C2 | 10/1985 | A61F/13/06 |
| DE | G 92 11 750.3 U1 | 4/1993 | A61F/13/06 |
| DE | 43 18 791 C2 | 12/1994 | A61F/13/06 |
| FR | 2364647 A1 | 4/1978 | A61F/13/06 |
| GB | 539243 | * 9/1941 | 602/65 |
| WO | 92/19187 | 11/1992 | A61F/13/06 |

* cited by examiner

Primary Examiner—Mickey Yu
Assistant Examiner—Denise Pothier
(74) Attorney, Agent, or Firm—Norris McLaughlin & Marcus

(57) ABSTRACT

Bandage for the ankle joint, consisting of an elongate strip and of a strap secured on the elongate strip, the first transverse edge of the elongate strip being arranged essentially vertically on the medial side of the ankle joint, the elongate strip being guided round the heel, across the lateral side of the ankle joint, across the back of the foot in the medial-plantar direction and across the sole of the foot in the lateral-plantar direction, the first transverse edge of the elongate strip being secured on the elongate strip itself, and the strap being joined to the second transverse edge, the said strap being guided from the lateral side of the sole of the foot across the back of the foot to the medial side of the ankle joint, round the heel to the lateral side of the ankle joint and across the lateral side of the ankle joint and being secured.

7 Claims, 4 Drawing Sheets

BANDAGE FOR THE ANKLE JOINT

The invention relates to a bandage for the ankle joint.

BACKGROUND OF THE INVENTION

Depending on their design and on the indications for which they are intended, orthopaedic bandages exert a fixing, guiding, bracing and/or supporting action on the extremities of the human body.

These medical bandages must have a shape which corresponds to the anatomical circumstances in order to be able to act externally on the human body with a form fit and a force fit.

Medical bandages of this kind are produced by cutting out blanks from planar material, for example neoprene, knitted fabrics or woven fabrics. The anatomically appropriate shape is obtained via the shape of the blanks or darts, for example with gussets, and subsequent joining together of the blanks, as is also customary in articles of clothing.

This joining together can be done by sewing, gluing or other conventional methods. The great disadvantage of these bandages is that the exact anatomical fit can be achieved only with difficulty and there are a large number of connection points, for example seams. These connection points change the properties of the material used, and there is the danger of pressure points on the skin.

Ankle joint orthoses or bandages are used preferably for the early functional treatment of recent fibular ligament ruptures and of mild and moderately severe tarsal distortions, and are also used in cases of chronic instability.

DE-A-38 40 714 discloses an ankle joint orthesis with a U-shaped support stirrup, the branches of which run together to form a bridge under the foot, reach upwards across the malleoli and are held together in their end region by a securing tape. The outer branch is in this case guided upwards laterally in front of its malleolus, and the inner branch opposite the outer branch is guided upwards in front of the Achilles tendon. Both branches, in the direction towards the bridge, are guided to a position in front of the heel, and, in the direction towards their ends, they extend upwards in such a way that they ascend laterally along the tibial ridges and approximately parallel to these, and a holding tape is arranged in the lower area of the branches, which holding tape extends from the one branch obliquely upwards across the instep to the other branch, and can be fastened thereon, engages above the malleoli about the Achilles tendon and, overlapping on the instep, ends on the other branch in a holding part. An ankle joint orthesis designed in this way is intended to prevent twisting, primarily in the lateral anterior direction, that is to say in the direction of a talipes equinus position. Since the U-shaped support stirrup of this ankle joint orthesis has its outer branch guided upwards laterally in front of the malleolus and has its inner branch guided upwards in front of the Achilles tendon, and is held together by a bridge running under the foot, the medial margin of the metatarsus is not gripped, with the result that the use of this ankle joint orthesis is limited.

DE-A-39 09 922 describes a foot fixation splint. This foot fixation splint is used in particular for the postoperative treatment of an injured ankle joint, with a foot part which surrounds the foot and to which there is joined a holding part extending upwards into the calf area and provided with closure straps. The holding part is in this case divided into two side parts which are joined to the foot part and are of cup-shaped design. The area of each side part covering the malleolus is provided with a window-type recess. The area of the Achilles tendon on the foot part and on the holding part is in this case left open. The adjustable and fixable tape-like closure straps are made of an inextensible material, and one closure strap is arranged on the foot part in such a way that it engages over the back of the foot and so fixes the first radius of the metatarsus against supinatory elevation. A foot fixation splint of this kind is intended, on the one hand, to ensure a satisfactory immobilization of the foot that is to be treated, and, on the other hand, to avoid the disadvantages of a plaster cast, since after injuries and operations involving the external ligament apparatus, the foot is often put in plaster in order to immobilize it, and postoperative treatment of operation wounds is not possible on account of a great many serious disadvantages. In the case of this foot fixation splint, the starting point is a U-shaped joint cuff with a full-surface sole part which covers the middle and front portions of the foot as far as the ball of the small toe, but which does not provide sufficient suppleness in the metatarsal area.

DE-C-43 18 588 likewise discloses an ankle joint orthosis consisting of a U-shaped joint cuff which is made of thermoplastic material and is composed of an outer malleolar splint and an inner malleolar splint. These malleolar splints are connected via a bridge running underneath the heel. The malleolar splints additionally have anatomically correct depressions for adaptation to the malleolar contours and for a correct anatomical fit. A further element of the orthesis is its metatarsal part, which is likewise made of thermoplastic material. This part of the orthesis runs obliquely under the sole of the foot, proximal to the capitula of metatarsals I-V, and is formed into a loop shape medially and laterally. The loops thus formed enclose the outer and inner margins of the foot. They guide the metatarsus on the one hand, and on the other hand serve for securing cross and transverse belts. The metatarsal part is in this case connected on the sole side by a bridge which is again made of thermoplastic material but is highly flexible. This bridge has the function of an articulation and acts analogously to an integral hinge. The pivot axis of this articulation formed in the highly flexible bridge runs from dorsomedial to anterolateral and forms with the long axis of the foot an angle of approximately 10°, in accordance with the anatomy of the lower part of the ankle joint.

SUMMARY OF THE INVENTION

The invention is based on the object of providing a bandage which is intended to be used in particular on the ankle joint and which as such is suitable for functional treatment of mild and moderately severe distortions of the tarsus and chronic instabilities, and with which a lateral and medial stabilization of the upper and lower part of the ankle joint is achieved, which reduces the risk both of inversion trauma and of eversion trauma.

This object is achieved by means of the bandage of the invention.

In accordance with the invention, the bandage for the ankle joint consists of an elongate strip and of a strap secured on the elongate strip. The first transverse edge of the strip is arranged essentially vertically on the medial side of the ankle joint. Starting from the first transverse edge, the elongate strip is guided round the heel, across the lateral side of the ankle joint, across the back of the foot in the medial-plantar direction and across the sole of the foot in the lateral-plantar direction. The first transverse edge of the elongate strip is secured, preferably stitched, on the elongate strip itself. In a preferred embodiment, the first transverse edge of the elongate strip is secured across its entire width on the elongate strip.

Also joined to the second transverse edge is the strap which is guided from the lateral side of the sole of the foot across the back of the foot to the medial side of the ankle joint, round the heel to the lateral side of the ankle joint and across the lateral side of the ankle joint and is secured.

This described type of arrangement of the elongate strip has the effect that the elongate strip is presented in a helical form, with approximately two thread turns, and is preferably stitched, so that a hollow interior is formed inside the bandage for receiving the foot. It is also possible, however, for the second transverse edge to be secured on the elongate strip.

In a preferred embodiment, the elongate strip has a transverse elasticity of 0% to 100%, in particular 5% to 30%, and a longitudinal elasticity of 30% to 250%, in particular 80% to 120%.

In a further preferred embodiment, the strap has a transverse elasticity of 0% to 100%, in particular 5% to 30%, and a longitudinal elasticity of 30% to 250%, in particular 50% to 100%.

It has proven particularly advantageous if the elongate strip is approximately 40 to 60 cm long and the strap is approximately 25 to 40 cm long, and if the elongate strip is approximately 8 to 12 cm wide and the strap is approximately 6 to 10 cm wide.

In a further preferred embodiment of the bandage, the second transverse edge is secured on the elongate strip at least with the proximal end and the strap is joined to the second transverse edge.

An embodiment is also preferred in which the second transverse edge is secured completely on the elongate strip and the strap is also joined to the second transverse edge.

The construction of the bandage according to the invention means that the elongate strip and the strap can be made of the same material and in particular can be punched out in a single blank. By means of the features of the bandage according to the invention, the said bandage effects a circular compression and a lateral and medial stabilization of the upper part of the ankle joint and the lower part of the ankle joint, which means that the risk of both inversion trauma and also eversion trauma is reduced.

The bandage permits a high degree of mobilization, as is necessary for functional treatment of the ankle joint; however, it also guarantees, by means of the defined, limited elasticity, a reliable stabilization of the injured ankle joint. The bandage is therefore particularly suitable for functional treatment of mild and moderately severe tarsal distortions and chronic instabilities.

The invention will be explained in greater detail with reference to four diagrammatic drawings showing an illustrative embodiment, namely the design for the left foot, without thereby wishing to restrict the invention unnecessarily. The design version of the bandage for the right foot is mirror-symmetrical to the first. In the preferred embodiment, the bandage can be converted from the left-foot version to the right-foot version by turning it inside out.

BRIEF DESCRIPTION OF THE DRAWINGS

It can be seen from

DETAILED DESCRIPTION

Figure 1:
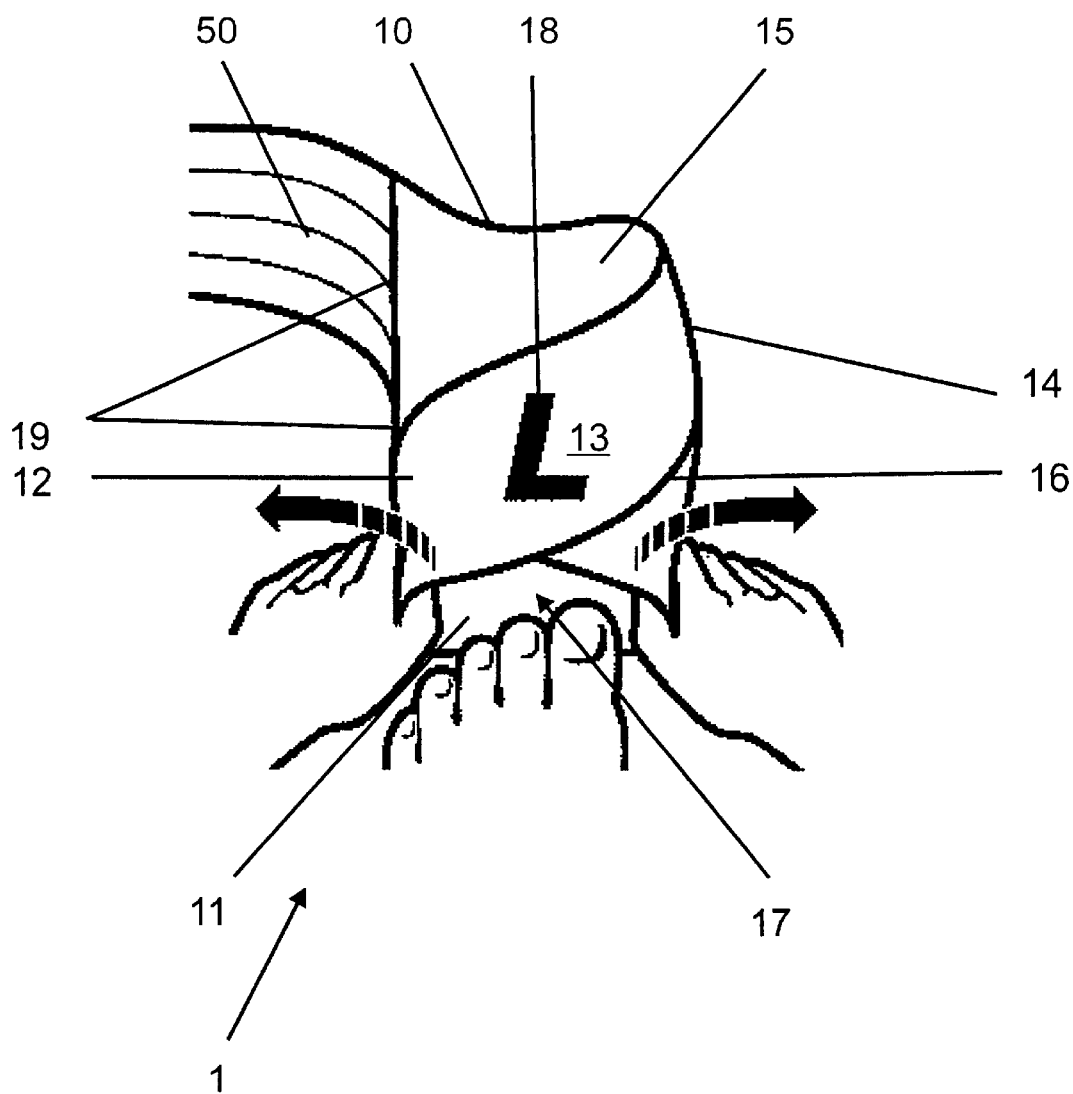
FIG. 1 the way of applying the bandage at the beginning, when the foot slips into the elongate strap, FIG. 2 to FIG. 4 the way of applying the strap being secured to the elongate strip.

FIG. 1 shows a particularly advantageous embodiment of the bandage 1 according to the invention for the ankle joint. The bandage 1 is accordingly made up of an elongate strip 10 and of a strap 50 secured to the elongate strip 10.

The first transverse edge 16 of the strip 10 is arranged essentially vertically on the medial side of the ankle joint. Starting from the first transverse edge 16, the elongate strip 10 is guided round the heel (section 11), across the lateral side of the ankle joint (section 12), across the back of the foot in the medial-plantar direction (sections 13 and 14) and across the sole of the foot in the lateral-plantar direction (section 15).

The first transverse edge 16 of the elongate strip 10 is secured along its entire width onto the first elongate edge 20 of elongate strip 10 itself.

The second transverse edge 19 at a point is stitched with the proximal end on the second elongate edge 21 of elongate strip 10. Furthermore, the strap 50 starts on the second transverse edge 19.

On that part of the bandage 1 which lies across the back of the foot (section 13), there is an indication, advantageously in the form of a label or an imprint 18, showing which ankle joint the bandage 1 is to be applied to, in this case showing a "L" for the left foot.

The special manner in which the bandage 1 is guided provides the opening 17 in which the malleolar region of the patient's leg is accommodated after the bandage 1 is applied.

FIG. 1 shows the way of putting the foot of the patient into the bandage 1. As shown like in FIG. 1 the bandage 1 has to be stretched at the opening 17 so that the foot can slip into that part of the bandage 1 which is formed like a sock.

Figure 2:
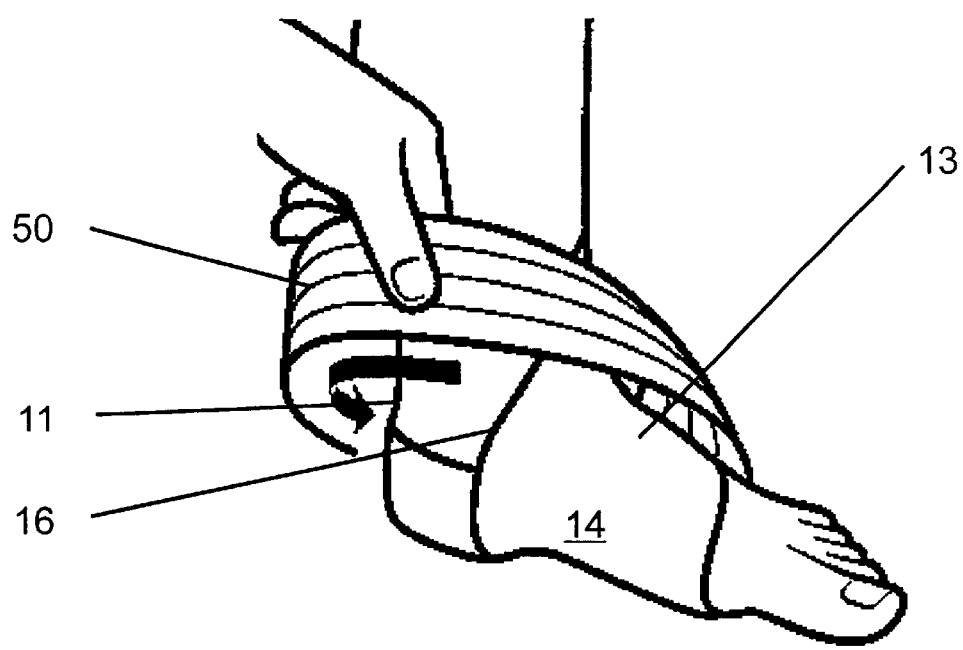
Figure 3:
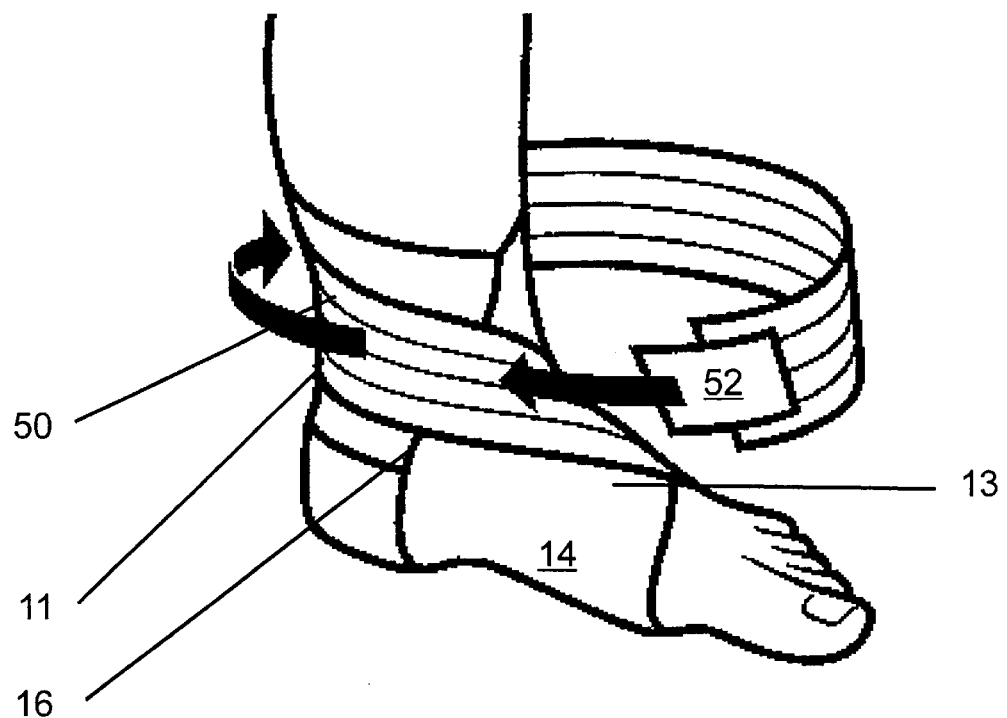
Figure 4:
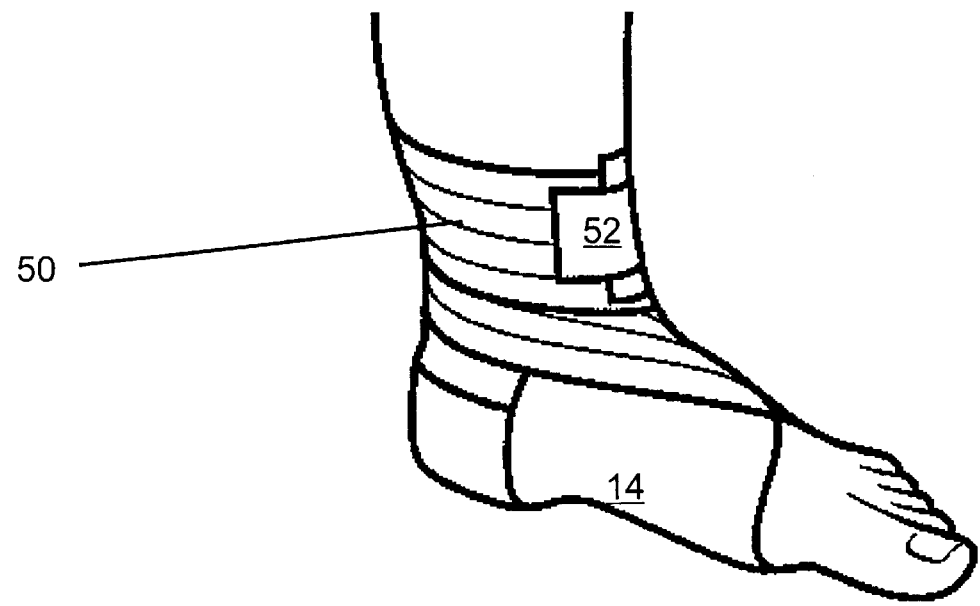

FIGS. 2 to 4 show the way of applying the strap 50 after the foot has slipped into that part of the bandage 1 built out of strip 10 which is formed like a sock.

As shown like in FIG. 2 the strap 50, starting from the lateral side of the sole of the foot, is guided across the back of the foot to the medial side of the ankle joint, round the heel to the lateral side of the ankle joint, and across the lateral side of the ankle joint and is secured.

A label 52 is preferably arranged on the strap 50, which label 52, in the manner of a velcro closure, itself ensures that the strap 50 is secured when the latter has been wound round the leg.

FIG. 4 shows the bandage 1 perfectly wrapped around the ankle joint with the secured end of the strap 50. Therefore, the strap 50 is guided once again around the leg of the patient.

Figure 5:
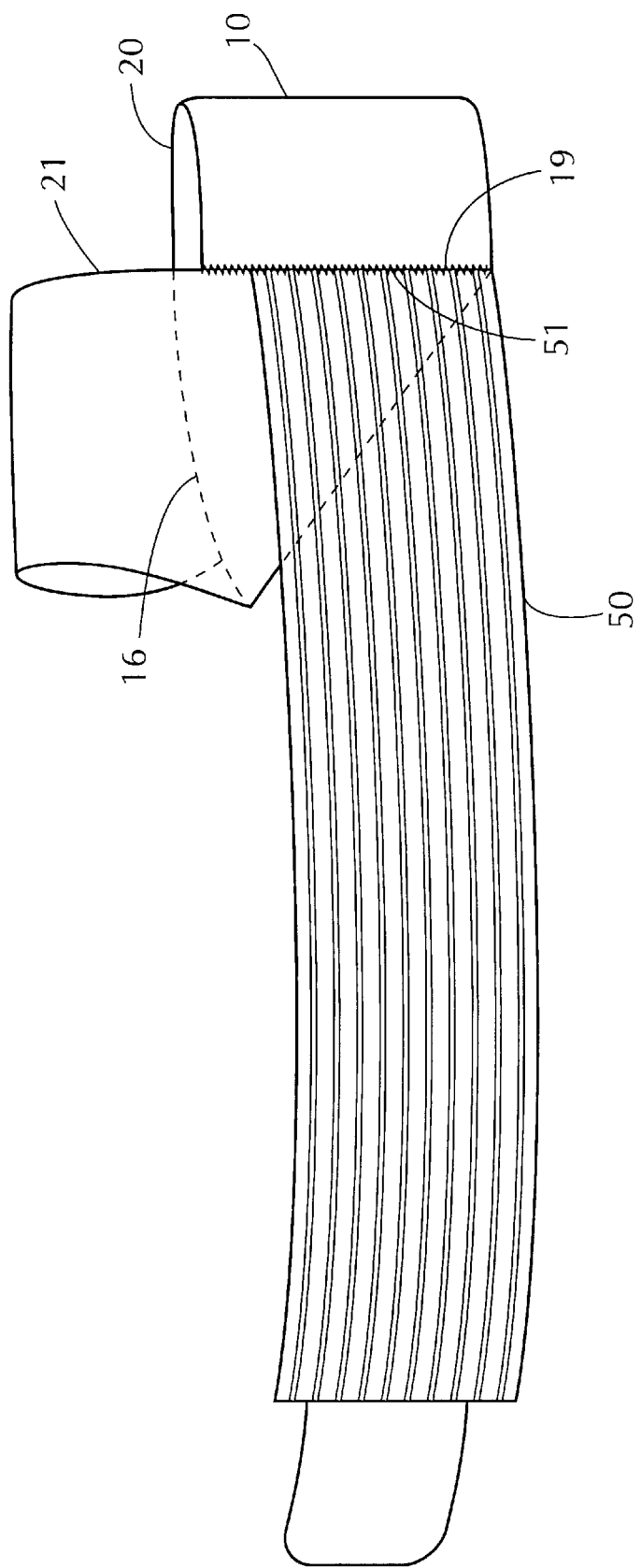
FIG. 5 shows the embodiment of the bandage of the present invention wherein the first transverse edge and the second transverse edge are both secured across their entire widths on the elongate strip and the strap is also joined to the second transverse edge.

FIG. 5 shows an embodiment of the invention wherein the first transverse edge (16) of the strip (10) is secured across its entire width to the first elongate edge (20) of the strip and the second transverse edge (19) of strip (10) is secured across its entire width to the second elongate edge (21) of the strip, and the first end (51) of strap (50) is joined to the second transverse edge (19) of the strip (1) as well as to the second elongate edge (21 ) of strip (10).

We claim:

1. A bandage for the ankle joint, consisting of an elongate strip having a first transverse edge, a second transverse edge, a first elongate edge and a second elongate edge; a strap having a first end and a second end; the second transverse edge of said elongate strip being secured to the first end of said strap, the first transverse edge of said elongate strip being secured to the first elongate edge of said elongate strip to form a loop and said second elongate edge of said elongate strip being secured at a point on said second transverse edge of said elongate strip, said elongate strip thereby being formed into a helical form having a hollow interior for receiving a human foot, an opening for accommodating the heel of such foot, a support for the back of the ankle of said foot, and the strap being adapted to be wrapped around said foot and ankle under tension, which tension is transmitted to said elongate strip, the second end of said strap being removably attachable to a surface of the wrapped strap itself, to secure the strap in said wrapped position.

2. Bandage according to claim 1, wherein the elongate strip has a transverse elasticity of 0% to 100% and a longitudinal elasticity of 30% to 250%.

3. Bandage according to claim 1, wherein the strap has a transverse elasticity of 0% to 100% and a longitudinal elasticity of 30% to 250%.

4. Bandage according to claim 1, wherein the elongate strip is approximately 40 to 60 cm long and the strap is approximately 25 to 40 cm long, and the elongate strip is approximately 8 to 12 cm wide and the strap is approximately 6 to 10 cm wide.

5. Bandage according to claim 1, wherein the first transverse edge of the strip is secured across its entire width to the first elongate edge of the strip and the second transverse edge of the strip is secured across its entire width to the second elongate edge of the strip and the first end of the strap is joined to the second transverse edge of the strip as well as to the second elongate edge of the strip.

6. Bandage according to claim 1, wherein the elongate strip and the strap are made of the same material and are punched of a single blank.

7. Bandage according to claim 1, which is convertable from a left-foot configuration to a right-foot configuration by turning it inside out.

\* \* \* \* \*

UNITED STATES PATENT AND TRADEMARK OFFICE
CERTIFICATE OF CORRECTION

PATENT NO. : 6,350,247 B2
DATED : February 26, 2002
INVENTOR(S) : Stefan Bodenschatz and Brigitte Rosenbaum It is certified that error appears in the above-identified patent and that said Letters Patent is hereby corrected as shown below:

<u>Title page,</u>
Item [56], U.S. PATENT DOCUMENTS, for the 7th entry change the Patent Number "3,766,385" to -- 3,763,858 --

<u>Column 6,</u>
Line 17, add the word -- out -- so claim 6 reads
-- Bandage according to claim 1, wherein the elongate
   strip and the strap are made of the same material
   and are punched out of a single blank. --

Signed and Sealed this

Fifteenth Day of April, 2003

JAMES E. ROGAN
*Director of the United States Patent and Trademark Office*